United States Patent [19]

Gruber et al.

[11] Patent Number: 5,200,525
[45] Date of Patent: Apr. 6, 1993

[54] ANTI-SEIZURE COMPOUNDS
[75] Inventors: Harry E. Gruber, San Diego; Paul J. Marangos, Encinnitas, both of Calif.
[73] Assignee: Gensia Pharmaceuticals, San Diego, Calif.
[21] Appl. No.: 301,453
[22] Filed: Jan. 24, 1989
[51] Int. Cl.$^5$ ........................................... C07D 233/46
[52] U.S. Cl. .............................. 548/311.7; 548/326.5
[58] Field of Search .................... 548/337, 336, 301
[56] References Cited
PUBLICATIONS
Fukuda et al., Chemical Abstracts, vol. 110, entry 95718s (1989).
Marumoto et al., Chemical Abstracts, vol. 108 entry 204978h (1988).
Taniyama et al., Chemical Abstracts, vol. 108, entry 6350j (1988).

*Primary Examiner*—John M. Ford
*Attorney, Agent, or Firm*—Lyon & Lyon

[57] ABSTRACT

A test method for identifying for and evaluating anti-seizure activity of candidate compounds is provided which shows superior sensitivity for adenosinergic activity and which is believed to be predictive of other adenosine releasing activities for the candidate compounds.

2 Claims, 7 Drawing Sheets

ANTI-SEIZURE COMPOUNDS

BACKGROUND AND INTRODUCTION TO THE INVENTION

The present invention is directed to a method of screening candidate compounds for anti-seizure activity, and which is concluded to be predictive of other adenosine releasing agent (ARA) therapeutic effects, such as anti-ischemic properties.

Procedures utilizing laboratory animals are set forth which have been found useful in screening candidate compounds for possible therapeutic potential. More specifically, described and claimed herein are procedures using agents which induce seizures in laboratory animals to screen and evaluate compounds for potential activity in preventing seizures in humans, and, thus, for usefulness as therapies for ischemic syndrome, and for seizure and related disorders and as anticonvulsant therapeutic agents.

The commonly-assigned, concurrently-filed and co-pending patent application "AICA Riboside Prodrugs", discloses the effect of certain adenosinergic agents in preventing induced seizures.

Previously, agents such as pentylenetetrazol (PTZ) have been used to induce seizures in convulsant systems which are used as models for anti-seizure activity. However, these systems are not sufficiently sensitive in measuring the anticonvulsive activity of compounds which are active in target seizure foci (i.e. areas of ATP depletion) but which have little or no effect on normal tissue.

During seizures certain neural cells fire abnormally. ATP catabolism is greatly accelerated in the abnormally firing cells leading to increased adenosine production. Adenosine has marked anticonvulsant effects and, thus, has been termed the brain's natural anticonvulsant. It appears to play a major role in the brain as an inhibitory neuromodulator; this action of adenosine is apparently mediated by certain ectocellular receptors. Adenosine has both post-synaptic and pre-synaptic effects. Among the documented effects of adenosine on nervous tissue are the inhibition of neural firing and of calcium dependent neurotransmitter release. Behaviorally, adenosine and its metabolically stable analogs have profound anticonvulsant and sedative effects.

As stated above, adenosine has been proposed to serve as a natural anticonvulsant with agents that alter its extracellular level acting as a modulator of seizure activity. Besides acting as a neuromodulator, adenosine is a potent vasodilator, an inhibitor of granulocyte oxygen free radical production, an antiarrhythmic. In fact, because of the many actions of adenosine, it has been called a "retaliatory molecule" released to protect cells against certain pathologic assaults.

Unfortunately, adenosine is toxic at concentrations that have to be administered systemically to a patient to maintain an efficacious extracellular therapeutic level at the target organ, and the administration of adenosine alone so far has been of limited therapeutic use. Likewise, since most cells in the body carry receptors for adenosine, the use of techniques that increase adenosine levels generally throughout the body can cause unwanted, dramatic changes in normal cellular physiology.

Most of the currently used antiseizure agents (including adenosine itself) exhibit side effects and toxicities or are without efficacity in many patients. There is a need for more effective anticonvulsant therapeutic compounds and strategies. An adenosinergic approach to anticonvulsant therapy appears promising. Accordingly, it is important to be able to both identify and evaluate candidate compounds for their ability to target seizure related foci in the brain without causing nonspecific effects in other tissue.

Homocysteine has been shown to be a central nervous system excitant at low concentrations and a convulsant at higher levels (Folbergrova, *Neuroscience* 6: 1405-1411 (1981); Wuerthele et al., *Life Sci.* 31:2683-2692 (1982); Dewhurst et al., *J. Neurochem.* 40:752-757 (1983)). Studies have shown that homocysteine at high doses causes tonic-clonic seizures. In fact, a considerable portion of homocysteineuric patients (a genetic disorder characterized by cystathione B synthase deficiency resulting in elevated serum levels of homocysteine) suffer from convulsive episodes (McKusick et al., in *Inherited Disorders of Sulfur Metabolism* (Carson, et al. ed.) pp. 179-203 (Churchill Livingstone, London, 1971); Mudd and Levy, in *The Metabolic Basis of Inherited Disease* (Stanbury, et al. ed.), pp. 458-503 (McGraw Hill, New York 1978)).

Homocysteine condenses with adenosine via the enzyme S-adenosylhomocysteine hydrolase ("SAH"; E.AC.3.3.1.1.), and the convulsant action of homocysteine may be in part a result of adenosine sequestration in brain. Recent data suggest that homocysteine can sequester adenosine that is released in response to electrical stimulation (McLlwain et al. *Neurochem. Int.* 7:103-110 (1985)). In addition, on the basis of tissue culture data, it has been proposed that increased brain homocysteine levels can result in a decrease of brain adenosine levels and that the mechanism of homocysteine induced seizures may be related to the sequestration of adenosine.

SUMMARY OF THE INVENTION

The present invention is directed to a simple, and rapid whole animal model which is useful in screening and evaluating candidate compounds for anti-seizure activity and in assessing activity for enhancing adenosine release.

Accordingly, the present invention is directed to a model for screening and/or evaluating candidate compounds for anticonvulsant activity which comprises administering a homocysteine delivery agent to laboratory animals which induces seizures.

This invention provides a method of screening candidate compounds for the ability to prevent seizures which comprises: (a) administering to an animal a test solution comprising the candidate compound to be screened; (b) administering to said animal a seizure-inducing composition comprising a homocysteine delivery agent and (c) determining if seizure is induced after administration to said animal of said seizure inducing composition. Although the candidate compound and seizure-inducing composition may be administered at the same time, it is preferred to administer the seizure-inducing composition a predetermined amount of time after the candidate compound.

In one aspect, the screening method of the present invention further comprises a first control group of animals to which neither said candidate compound or said seizure inducing composition is administered, a second group of animals to which only said seizure inducing composition is administered, and a third group of animals to which both candidate compound and seizure inducing composition is administered.

Suitable homocysteine delivery agents for use according to the method of the present invention include agents which are capable of delivering homocysteine to the brain, i.e., are capable of crossing the blood-brain barrier in a sufficient concentration to induce seizure and include homocysteine itself, as well as esters and salts thereof. Preferred homocysteine delivery agents include L-homocysteine thiolactone (HTL) and salts thereof. Racemic mixtures, as well as pure stereoisomers may be used. Since it is believed that the L-isomer is the biologically active stereoisomer, if a racemic mixture is used, the dose of the homocysteine delivery agent must be adjusted accordingly.

In a preferred embodiment of the method of the present invention, said seizure inducing composition comprises at least about 200 mg/kg HTL, more preferably from about 300 to about 2000 mg/kg HTL. Particularly preferred are seizure inducing compositions which comprise from about 750 to 1000 mg/kg HTL. Preferred doses for other homocysteine delivery agents comprise amounts approximately equimolar (of the L-isomer) to the preferred doses of HTL.

The seizure inducing composition is selected to be of sufficient strength to induce seizures in essentially all animals to which only the seizure inducing composition is administered.

Animals who do not have seizures within about six times the latent period for the homocysteine delivery agent used (for HTL about two hours, six times the latent period of about twenty minutes) are determined to be seizure-inhibited.

Candidate compounds for which at least about 30% of the test solution treated animals are determined to be seizure inhibited are considered to show seizure-inhibiting activity. Candidate compounds for which at least 90% of the test solution treated animals are determined to be seizure inhibited are considered to show very significant seizure inhibiting activity. A prolongation of the seizure latency by 50% indicates minimal antiseizure activity (non-seizing animals are counted as a two hour latency). Prevention of homocysteine-induced mortality is also indicative of efficacy.

Among other factors, the present invention is based on our finding that this evaluation and screening method using homocysteine-induced seizures constitutes a reliable system of evaluating candidate compounds whose activity in inhibiting seizures is not readily detected using the PTZ-induced seizure model. In particular, the method of the present invention will distinguish those anti-seizure compounds having adenosine agonist-like activity which is not well detected using the PTZ model.

DETAILED DESCRIPTION OF THE INVENTION

According to a preferred embodiment of the method of the present invention, the animals being tested were preinjected with a first injection comprising either a test solution containing the candidate compound in carrier or a control which contained only carrier. Various lab animals may be used, but mice are particularly suitable due to their size (i.e., less candidate compound needed for testing) and the commercial availability of inbred mouse strains with well-characterized genetic and behavioral traits. To obtain more reliable results, it is preferable to inject a group of animals with a particular candidate compound solution (or dose of the candidate compound) or a control solution. Groups of 6 to 8 generally provide a sufficiently large sample for statistically reliable test results. Of course, larger groups may increase the statistical precision of such results, but overly large samples may unnecessarily increase the effort and expense of the screening tests. Preferably, the candidate compound is administered intraperitoneally. The seizure-inducing composition is preferably administered subcutaneously.

At a specific time interval (generally between 15 minutes to several hours) after the first injection of test solution or control solution, a second injection comprising an aliquot of homocysteine delivery agent in carrier is administered. Animals receiving first and second injections comprising carrier are used as controls.

After the second injection, it is preferable to isolate the animals in separate cages. The animals are observed for onset of seizure.

Animals were scored as being fully protected from a seizure if they failed to seize for a period of about 6 times the carrier latency period following a second injection comprising the homocysteine delivery agent. When HTL is used as the homocysteine delivery agent, the period is about 1 to about 3 hours, since for HTL the carrier control latency is about 20 minutes. Seizures noted are either clonic or clonic-tonic in nature and may vary in severity from forelimb clonus to full tonic extension of hind limbs and forelimbs. The number of seized animals, seizure latency and the mortality rate of animals having seizures are recorded.

For a comparison of evaluation methods, tests using PTZ as the seizure-inducing agent may be run following the above-described procedure. However, due to the more rapid onset of seizures induced by PTZ, an animal is scored as fully protected if it fails to seize one hour after injection of PTZ (carrier control seizure latency of about 4 minutes). A comparison of models using homocysteine-induced seizures with that using PTZ-induced seizures demonstrated that the homocysteine model is superior for the screening and/or evaluation of candidate compounds for adenosinergic activity.

We have found that in animals receiving injections of control solution at a dose of 850 mg/kg, HTL produces seizures in 100% of mice with a latency of about 1150 seconds. These are full clonic-tonic seizures with approximately 30% mortality. Other homocysteine delivery agents will produce seizures at approximately equimolar doses.

Figure 6A:
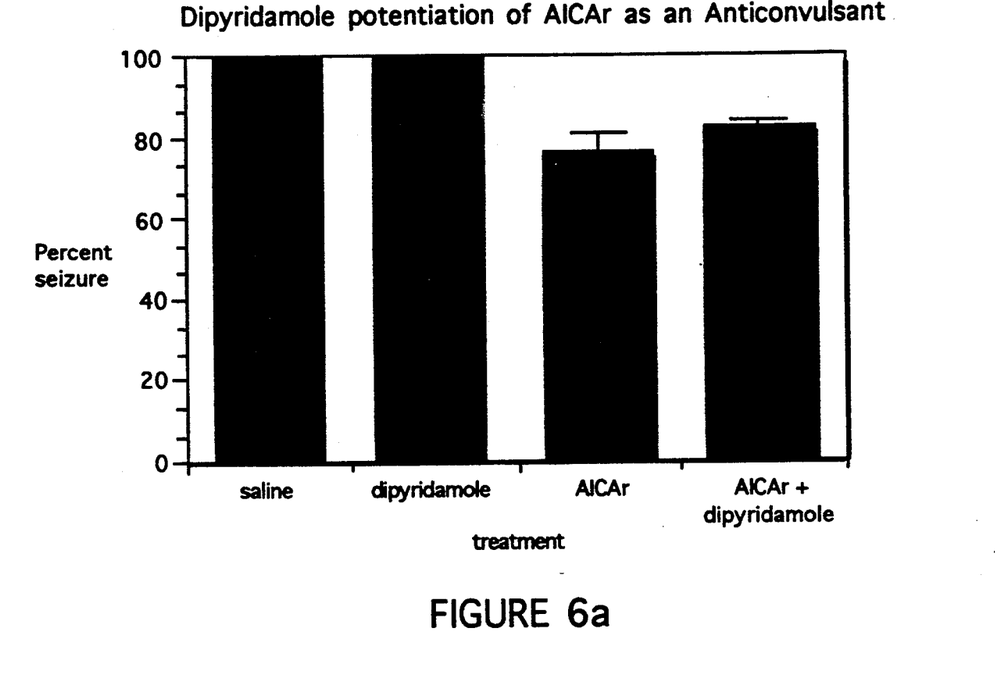
FIG. 6a and 6b depicts the effect of adenosine uptake blockers (mioflazine and dipyridamole) on AICA riboside activity in inhibiting seizures.
Figure 6B:
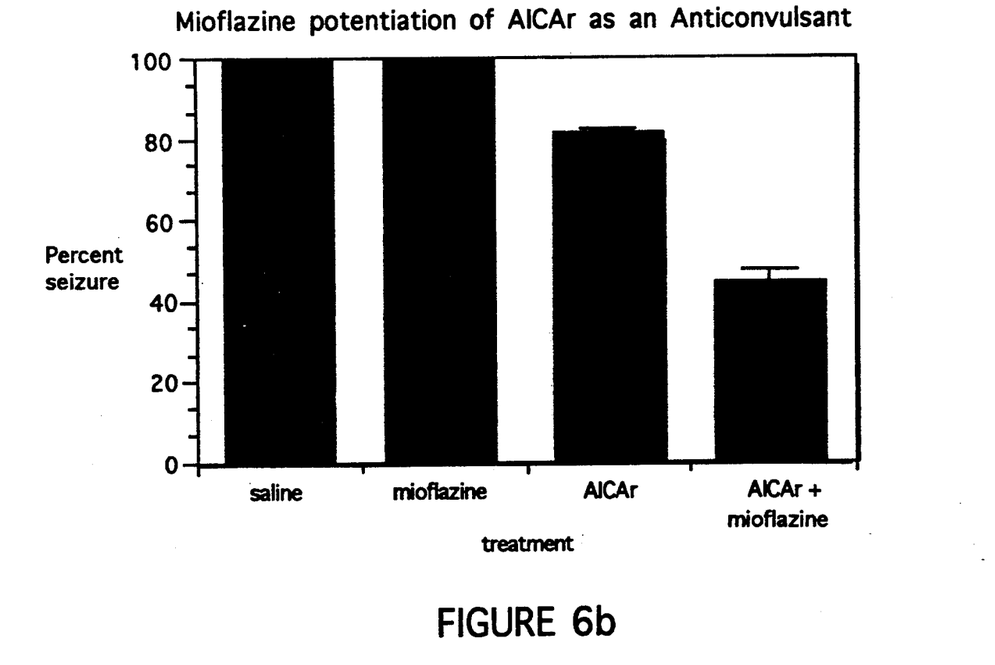

Studies using the method of the present invention have indicated that the administration of certain adenosine uptake blocking agents such as mioflazine, may potentiate the activity of adenosinergic agents such as AICA riboside in preventing homocysteine-induced seizures even though such adenosine uptake blocking agents themselves have no inherent antiseizure activity. (See e.g., Example 6 and FIG. 6.)

One compound found to have promising anti-seizure activity when evaluated by the test method of the present invention was carbocyclic AICA riboside ("($\pm$)-5-Amino-1-[$\bar{A}$-2$\acute{A}$-Adihydroxy-4'$\bar{A}$-(hydroxymethyl)cyclopentyl]imidazole-4-carboxamide"). Carbocyclic AICA riboside can be prepared by the method described in Arita, et al., *Nucleic Acids Research Symposium Series* 12:25–28 (1983) which reports the making of this compound for use as an intermediate. Carbocyclic AICA riboside may be administered in a prodrug form, that is as a derivative of carbocyclic AICA riboside which, after introduction into the body of an animal, is metabolized to its active carbocyclic AICA riboside form. Since carbocyclic AICA riboside has shown activity in the test method of the present invention which we believe to be predictive of ARA activity, we have concluded that carbocyclic AICA riboside will exhibit other ARA activities such as those shown by AICA riboside and its prodrugs as described in the commonly assigned and concurrently-filed U.S. patent application "AICA Riboside Prodrugs".

CARBOCYCLIC AICA RIBOSIDE COMPOUNDS

The present invention also provides a novel class of prodrugs of carbocyclic AICA riboside.

These prodrug compounds comprise a modified carbocyclic AICA riboside having an carbocyclic AICA ribosyl moiety which comprises an AICA moiety and a cyclopentyl moiety and at least one hydrocarbyloxycarbonyl or hydrocarbylcarbonyl moiety per equivalent weight of carbocyclic AICA ribosyl moiety.

Carbocyclic AICA riboside may be chemically modified to yield a carbocyclic AICA riboside prodrug wherein one or more of the hydroxyl oxygens of the cyclopentyl moiety (i.e. 2'-, 3'- or the oxygen of the 4'-hydroxymethyl group) is substituted with a hydrocarbyloxycarbonyl or hydrocarbylcarbonyl moiety.

These compounds function as prodrugs of carbocyclic AICA riboside and are better absorbed from the gastrointestinal system and are better able to cross the blood-brain barrier than carbocyclic AICA riboside itself. It is believed that the modifying ester side groups allow for improved capabilities in absorption from the gastrointestinal system and in reduced first pass metabolism, as well as making more drug available for crossing the blood-brain barrier. As the prodrug molecule approaches or reaches the active site, intact modifying groups can be endogenously cleaved to regenerate carbocyclic AICA riboside.

The prodrug compounds of the present invention are useful in treating a variety of clinical condition where increasing extracellular levels and release of adenosine would be beneficial. Accordingly, the present invention is directed to the prophylactic and affirmative treatment of such conditions as stroke, Alzheimer's disease, homocysteineuria, skin flap and reconstructive surgery, ischemic syndrome and other seizure-related conditions using these prodrug compounds. This invention is also directed to pharmaceutical compositions comprising an effective amount of a prodrug compound of the present invention in a pharmaceutically acceptable carrier.

In one aspect, the present invention is directed to novel prodrug compounds which comprise a modified carbocylic AIA riboside having a carbocyclic AICA ribosyl moiety which comprises an AICA moiety and a cyclopentyl moiety and at least one hydrocarbyloxycarbonyl or hydrocarbylcarbonyl moiety, or combinations thereof, per equivalent weight of carbocyclic AICA ribosyl moiety. It is preferred that said prodrug does not have two or more of the same hydrocarbylcarbonyl moieties per equivalent weight of carbocyclic AICA ribosyl moiety. Preferred prodrug compounds include those where at least one of the hydroxy oxygens of the cyclopentyl moiety is substituted with a hydrocarbyloxycarbonyl or hydrocarbylcarbonyl moiety. Particularly preferred are compounds wherein at least one hydroxy oxygen is substituted with a hydrocarbyloxycarbonyl moiety. One preferred class of prodrug compounds comprise compounds wherein either the 3'-hydroxyl oxygen or the hydroxyl oxygen of the 4'hydroxymethyl group of the cyclopentyl moiety is substituted with a hydrocarbyloxycarbonyl moiety.

Preferred carbocylic AICA riboside prodrug compounds of the present invention include those having the following formula:

wherein $X_1$, $X_2$, and $X_3$ are independently hydrogen or wherein $R_1$ and $R_2$ are independently hydrocarbyl preferably of from 1 to about 24 carbon atoms, or two of $X_1$, $X_2$ and $X_3$ taken together form a cyclic carbonate group, provided that not all of $X_1$, $X_2$ and $X_3$ are hydrogen. It is preferred that not all of $X_1$, $X_2$ and $X_3$ are acetyl, propionyl or benzoyl or if one of $X_1$, $X_2$, and $X_3$ is hydrogen, the other two are not both benzoyl. Preferred $R_1$ and $R_2$ groups include lower alkyl groups, especially preferred are those having at least one secondary carbon atom. Hydrocarbyl groups having more than 24 carbon atoms may be used and are considered to be within the scope of the present invention.

Preferred compounds include those having one or two ester groups. More preferred are those having one ester group. Especially preferred are compounds having an ester group at either the 3'-position or attached to the 4'-methyl of the cyclopentyl ring.

One preferred class of compounds is the carbonate esters.

Particularly preferred are compounds wherein $X_1$ or $X_3$ is

In one especially preferred compound, $X_1$ and $X_2$ are hydrogen and $X_3$ is isobutoxycarbonyl.

The term "hydrocarbyl", as used herein, denotes an organic radical composed mainly of carbon and hydrogen which may be aliphatic (including alkyl, alkenyl and alkynyl groups and groups which have a mixture of saturated and unsaturated bonds), alicyclic (carbocyclic), aryl (aromatic) and combinations thereof; and may refer to straight chain and branched-chain or cyclic structures or to radicals having a combination thereof; as well as to radicals substituted with halogen atoms or heteroatoms, such as nitrogen, oxygen and sulfur, and their functional groups (such as amino, alkoxy, aryloxy, lactone groups and the like) which are commonly found in organic compounds and radicals.

The preferred carbonate ester and acyl ester carbocyclic AICA riboside prodrug compounds of the present invention may be conveniently prepared according to the following reaction scheme:

wherein $X_1$, $X_2$, $X_3$, $R_1$, and $R_2$, are as defined in conjunction with formula (I).

Reaction (1) is carried out by combining II, carbocyclic AICA riboside, and III, the appropriate acid chloride or chloroformate, in solvent. As noted above, the preparation of carbocyclic AICA riboside has been reported. The acid chloride may be conveniently prepared by conventional procedures such as reaction of the corresponding acid with thionyl chloride; some acid chlorides are commercially available. Many chloroformates are commercially available; also, the chloroformates may be conveniently prepared by conventional procedures known to those skilled in the art by the reaction of phosgene with the appropriate alcohol. Reaction (1) is conducted at a temperature of from about $-10°$ C. to about $5°$ C., preferably from about $5°$ C. to about $0°$ C. and is generally complete within about 2 to about 4 hours. For ease of handling, the reaction is carried out in solvent. Suitable solvents include dimethylformamide (DMF), pyridine, methylene chloride and the like. For convenience, the reaction is carried out at ambient pressure. The reaction product(s) are isolated by conventional procedures as column chromatography, crystallization and the like. As may be appreciated, the reaction may result in a mixture of products, mono, di, and tri-esters at the 2'-, 3'- and/or 4'-hydroxymethyl positions of the cyclopentyl moiety. The product esters may be separated by conventional procedures such as thin layer chromatography (TLC), high pressure liquid chromatography (HPLC) column chromatography, crystallization, and the like which are well known to those skilled in the art.

The 4'-hydroxymethyl-monoesters may be conveniently prepared according to the following reaction scheme to give an intermediate blocked at the 2' and 3' positions.

wherein $X_a$ is and DbAg is a deblocking agent.

Reaction (2) is conducted by combining II, IV, V and VI. Although the reactants may be combined in any order, it may be preferred to add II to a mixture of IV, V and VI. The reaction is carried out at a temperature of about $10°$ C. to about $25°$ C., preferably from about $15°$ C. to about $25°$ C. and is generally complete within about 5 hours. Intermediate VI is isolated by conventional procedures.

Reaction (3) is the reaction of intermediate VII with the appropriate acid chloride or chloroformate and is carried out as described in connection with Reaction (1).

Reaction (4) is an optional step to remove, if desired, the cyclic blocking group from the 2' and 3' positions. It is carried out by reacting with IX, the appropriate deblocking agent. Suitable deblocking agents include H+ resin in water/acetone, tetraethyl-ammonium fluoride/THF, acetic acid/water, and the like. Such deblocking reactions are conventional and well known to those skilled in the art.

Mixed ester compounds (those having both acyl ester and carbonate ester groups) may be conveniently prepared by first reacting carbocyclic AICA riboside with the appropriate acid chloride according to Reaction (1) to add the acyl ester group and then reacting the acyl ester-substituted compound with the appropriate chloroformate according to Reaction (1) to obtain the mixed ester.

To assist in understanding the present invention, the results of a series of experiments follow. The following examples relating to the present invention should not, of course, be construed as specifically limiting the invention, and such variations of the invention, now known or later developed, which would be within the purview of one skilled in this art are to be considered to fall within the scope of this invention as hereinafter claimed.

EXAMPLE 1

Induction of Seizures Using HTL

Animals used were male Swiss Webster mice weighing 21-30 grams (Charles River Breeding Labs, Wilmington, Mass.). All animals were adapted to the laboratory for at least 5 days prior to use.

All solutions to be injected were prepared as a single injection cocktail at a concentration such that 1 ml per 100 g of body weight yielded the desired dose. The solutions were compounded as follows: Homocysteine-Thiolactone-HCl (HTL-HCl) (Sigma Chemical Company, St. Louis, Mo.) was dissolved in distilled water and the pH adjusted to 6.7 with NaOH. Pentylenetetrazol (PTZ) was dissolved in 0.9% saline. Candidate compounds, such as AICA riboside (Sigma), when used alone were dissolved in distilled water. All solutions containing Mioflazine (Janssen Pharmaceuticals) were prepared at a final DMSO concentration of 10-15% as were the Dipyridamole (Sigma) solutions. N-ethylcarboxamide adenosine, (Sigma) and Flunitrazepam (Hoffmann La Roche) injections were prepared in a final ethanol concentration of 0.2%. In all cases carrier control solutions of carrier were injected that were matched for both tonicity and solvents to the test solutions. All test and control solutions were injected via a bolus, I.P., using a 27 gauge needle. HTL and PTZ were injected subcutaneously in the upper back of the animal.

Animals were preinjected intraperitoneally with either control solution containing only carrier or test solution containing candidate compound and carrier in groups of 6-8 per test solution or control. The seizure inducing composition was injected subcutaneously at a specific time interval thereafter (ranging from 15 minutes to several hours, most experiments utilized a 30 minute interval). After injection of the seizure inducing composition animals were isolated in separate cages and observed for the onset of a seizure. In most experiments, animals were scored as being fully protected from a seizure if they failed to seize for a period of 1-3 hours following homocysteine thiolactone (HTL) injections (carrier control seizure latency about 20 minutes) and 1 hour after PTZ administration (carrier control seizure latency of 4 minutes). Seizures noted were either clonic or clonic-tonic in nature and varied in severity from forelimb clonus to full tonic extension of hind limbs and forelimbs. In all experiments the seizure latency was also noted as was the mortality rate in animals having seizures. The overt character of both the PTZ and HTL seizures were quite similar although the latency of the former was markedly shorter.

EXAMPLE 2

Dose Response Relationships for HTL Induced Seizures

A study of the dose response relationships for HTL induced seizures was performed by administering a series of doses of HTL to mice according to the procedure described in Example 1. Each group contained 8 animals.

Figure 1:
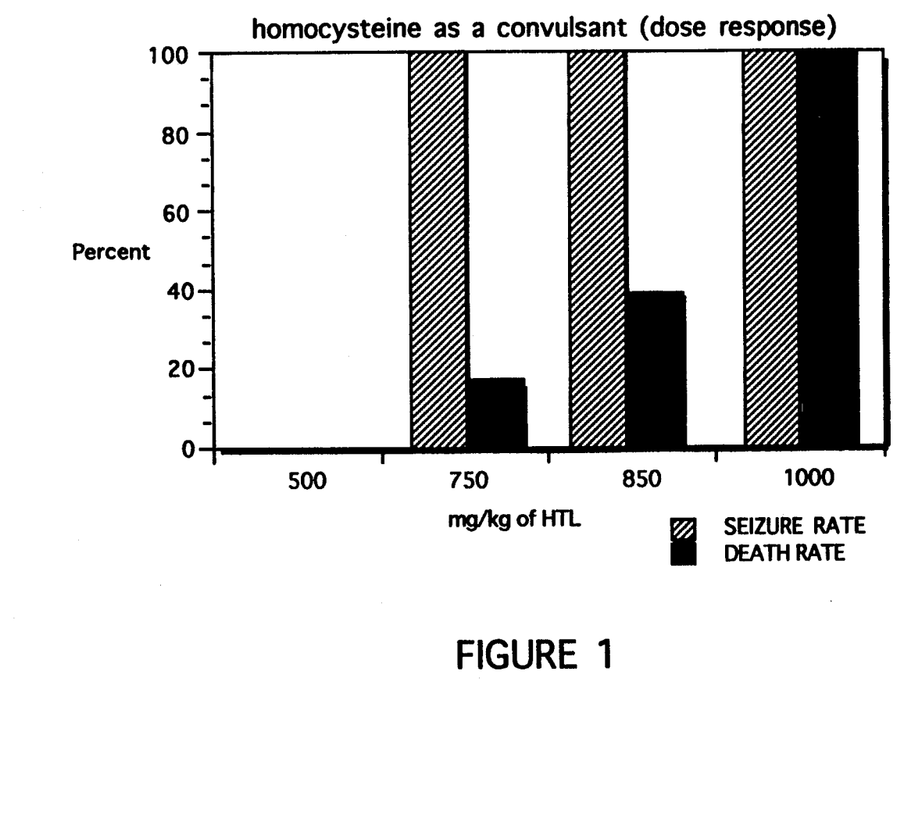
FIG. 1 depicts the dose response of HTL in inducing seizures.

In determining the dose response relationships for HTL-induced seizures, tonic-clonic seizures were not observed until a dose of 750 mg/kg at which dose virtually all animals had seizures and the mortality rate was about 20% (FIG. 1). The seizure latency was about 20 minutes with a rather broad variation. At 850 mg/kg of HTL again all animals routinely had tonic-clonic seizures with similar average latencies but much less variance when compared with the 750 mg/kg dose. Mortality at this dose was about 30% compared with 100% mortality at 1000 mg/kg. A dose of 850 mg/kg was chosen for most of the subsequent studies, since this dose gave reproducible results with relatively consistent latencies.

The seizure latencies were $1209 \pm 159$ sec at 750 mg/kg, $1289 \pm 32$ sec at 850 mg/kg, and $576 \pm 10$ sec at 1000 mg/kg.

EXAMPLE 3

Seizure Inhibitory Potential of Adenosinergic Agents

Rats were treated to induce seizures according to the procedures described in Example 1. The time interval between administration of drug and seizure inducing composition was 30 minutes. Each group contained 8 animals.

Figure 2:
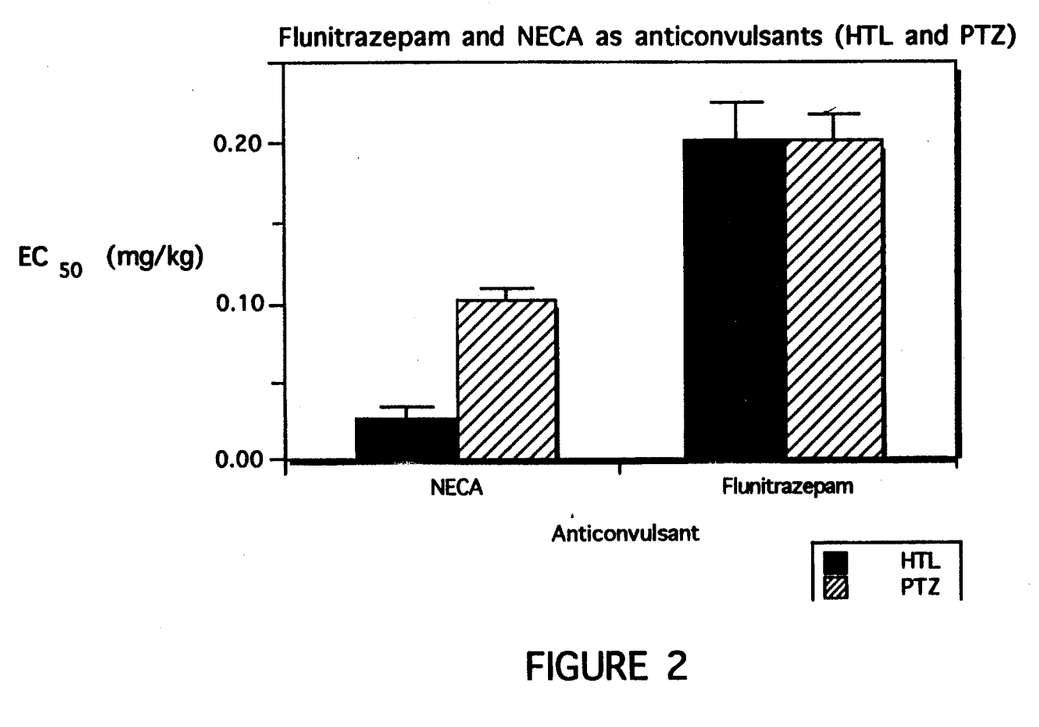
FIG. 2 depicts the activity of flunitrazepam and NECA in inhibiting PTZ and HTL induced seizures.

In an effort to evaluate the inhibitory potency of adenosinergic agents on HTL induced seizures we determined the anticonvulsant potency of N-ethylcarboxamide adenosine (NECA) against HTL and PTZ induced seizures (FIG. 2). NECA was very potent in both convulsant paradigms but was about 4 fold more potent as a blocker of HTL seizures ($EC_{50}$ of 0.025 vs. 0.100). A similar evaluation with flunitrazepam (a benzodiazepine) showed virtually identical potency of this drug as an inhibitor of seizures induced by both convulsants. Accordingly, the homocysteine model (using HTL) was more sensitive in evaluating adenosinergic agents in comparison to the PTZ model. In both PTZ and HTL seizure paradigms NECA proved to be markedly more potent than flunitrazepam (8 fold and 2 fold for HTL and PTZ seizures respectively). Data presented are means ±SEM.

EXAMPLE 4

Inhibitory Potential of AICA Riboside

Tests of susceptibility of induced seizures to various doses of AICA riboside were performed according to the procedure described in Example 1. AICA riboside was administered 30 minutes prior to HTL administration. Each group contained 8 animals.

Mice receiving up to 1.25 grams/kg of AICA riboside demonstrated no sedation or other behavioral alterations or apparent toxicity after several weeks. The doses of AICA riboside used in this study were therefore without apparent effects.

Figure 3:
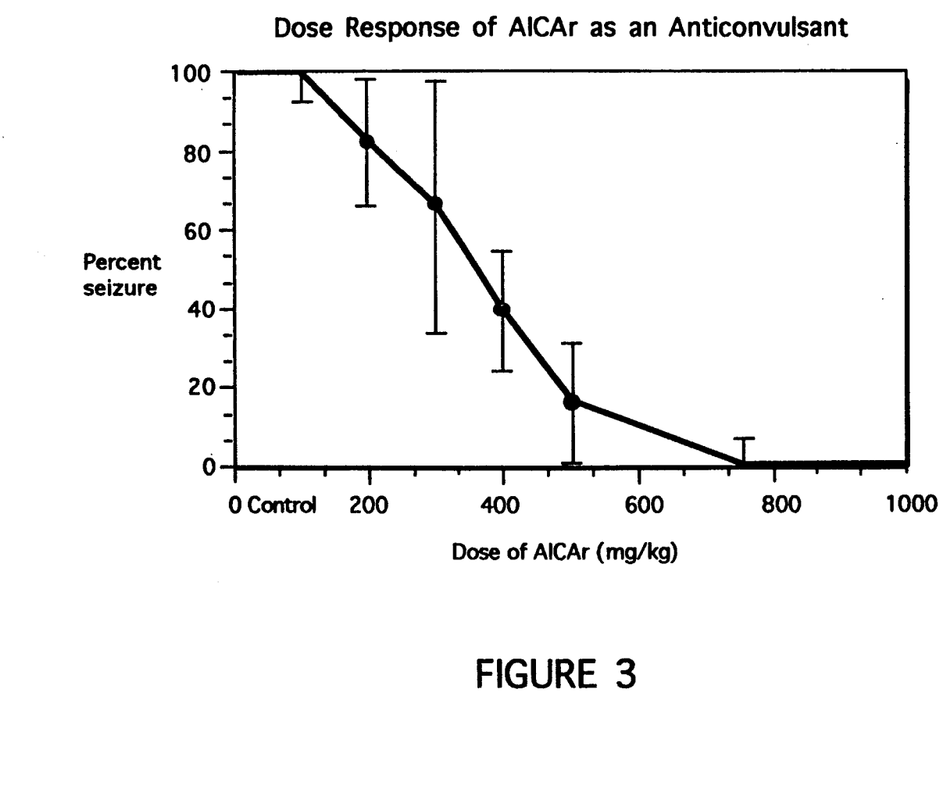
FIG. 3 depicts the dose response of AICA riboside in inhibiting HTL induced seizures.
Figure 4:
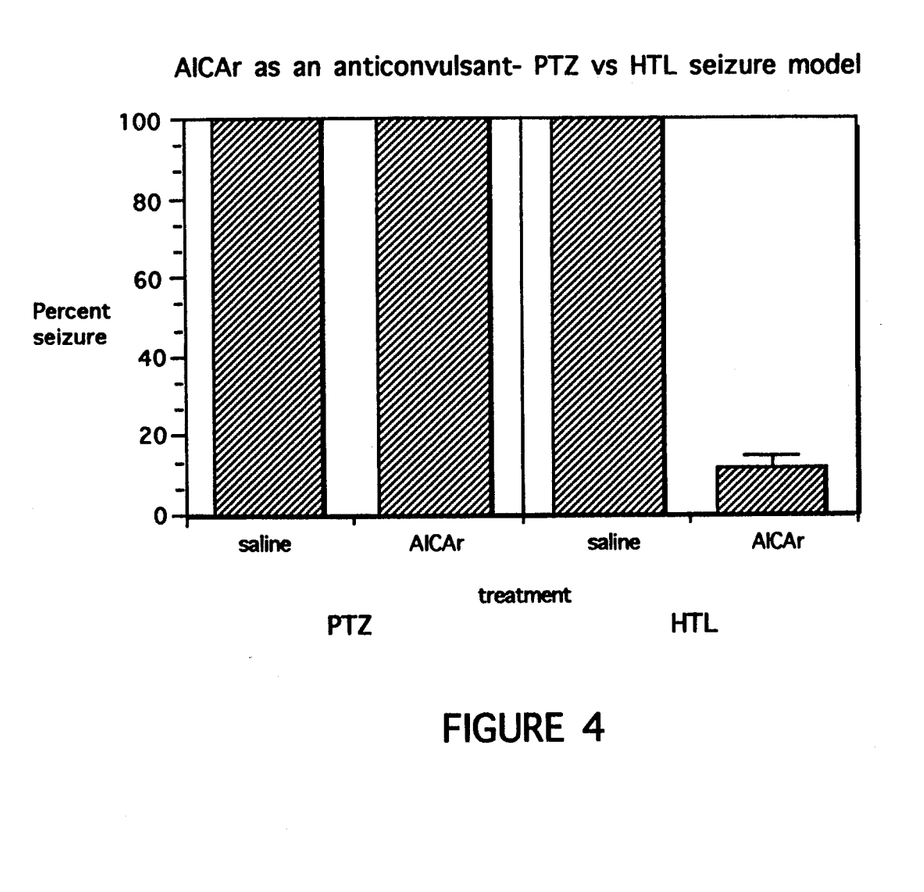
FIG. 4 depicts a comparison between HTL and PTZ in evaluating the anti-seizure activity of AICA riboside.

The inhibitory potency of AICA riboside as an anticonvulsant in the HTL seizure system is shown in FIG. 3. Results are averages ($\pm$S.D.) of 3 separate experiments. Doses of 300 mg/kg routinely show a significant anticonvulsant effect with a dose of 750 mg/kg affording complete protection in most animals. Comparing the anticonvulsant properties of AICA riboside (dose 750 mg/kg) against HTL (dose 850 mg/kg) and PTZ (dose 65 mg/kg) induced seizures (FIG. 4) clearly demonstrates that again as seen in FIG. 2 the HTL induced seizures were apparently more susceptible to adenosine inhibition and, thus, the homocysteine model exhibited a superior sensitivity in evaluating the activity of adenosinergic agents. In another experiment, it was reproducibly shown that doses of about 1 gram/kg of AICA riboside marginally increased the latency of PTZ induced seizures in mice. A frank anticonvulsant effect was not observed. Similar results were also obtained with caffeine induced seizures (dosage level 290 mg/kg of caffeine).

EXAMPLE 5

Duration of Anti-Seizure Activity for AICA Riboside

A study of the duration of anti-seizure activity for AICA riboside was performed by varying the times when HTL and AICA riboside were administered following the procedures described in Example 1. The AICA riboside dose was 750 mg/kg; the HTL dose was 850 mg/kg. Six to eight animals were used in each group.

Figure 5:
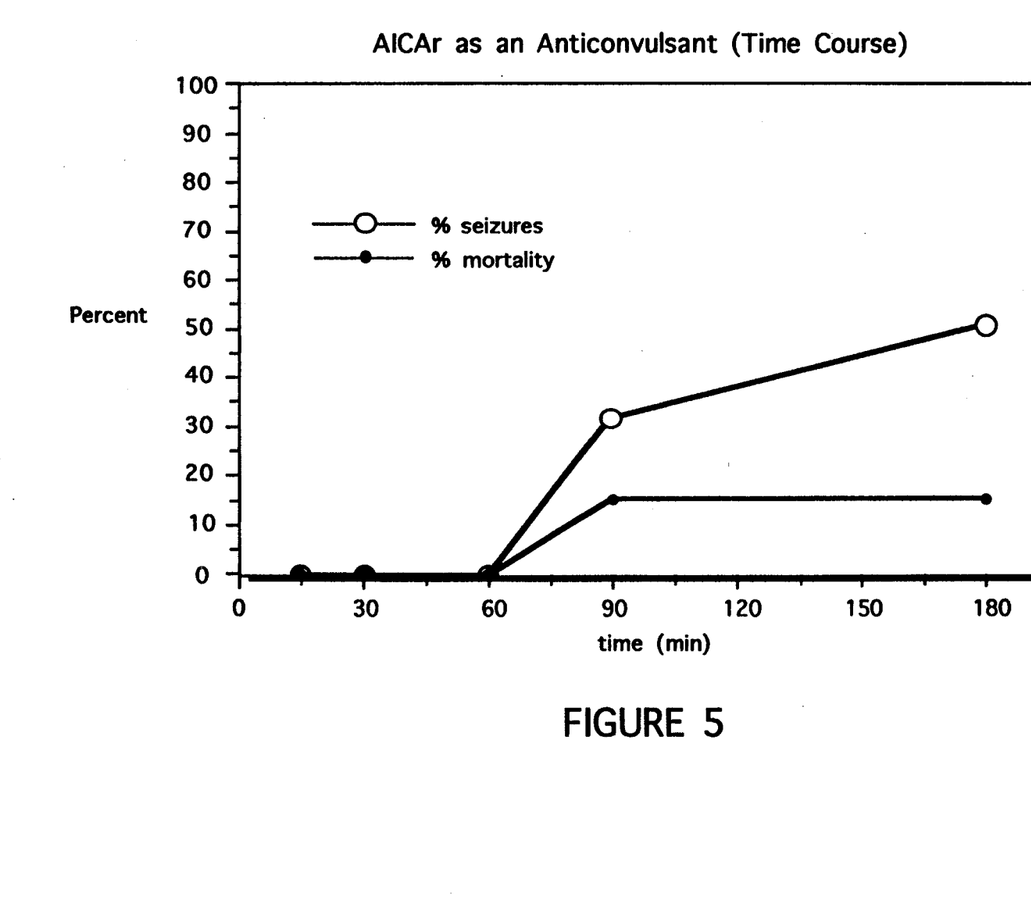
FIG. 5 depicts the activity relationship between time of administration of AICA riboside and inhibition of seizures.

To determine the duration of action of AICA riboside, we conducted an experiment where the time between AICA riboside and HTL administration was varied. As seen in FIG. 5, AICA riboside was fully active as an anticonvulsant from a period of 15 to 60 minutes after which time the anticonvulsant potency decreased.

EXAMPLE 6

Effect of Adenosine Blockers on AICA Riboside Action

Studies were done on the effect of adenosine uptake blockers on the anti-seizure activity of AICA riboside according to the procedures described in Example 1. The AICA riboside dose was 300 mg/kg, dipyridamole dose was 5 mg/kg and mioflazine dose was 2 mg/kg. Results are presented as means $\pm$SEM.

Since the anticonvulsant action of AICA riboside was thought to involve an increase in adenosine at the seizure foci, it was deemed appropriate to evaluate the effect of adenosine uptake blockers on its anticonvulsant effect. FIG. 6 shows the effect of either mioflazine or dipyridamole on the anticonvulsant effect of AICA riboside. A dose of 2 mg/kg of mioflazine markedly potentiated the protective effect of AICA riboside. This dose of mioflazine had no effect by itself on HTL induced seizures. Dipyridamole at doses of 5 mg/kg was without significant effect in this same experimental paradigm (FIG. 6) as was soluflazine (up to 50 mg/kg). Nitrobenzylthioinosine (Sigma) was also without appreciable effect in potentiating the activity of AICA riboside at doses up to 5 mg/kg. Mioflazine was the only one of these adenosine uptake blockers which is believed to cross the blood-brain barrier.

EXAMPLE 7

Evaluation of Carbocyclic AICA Riboside for Antiseizure Activity

Carbocyclic AICA riboside was tested for anti-seizure activity according to the method described in Example 1. Carbocyclic AICA riboside was administered at a dose of 400 mg/kg. HTL was administered at a dose of 950 mg/kg.

Figure 7:
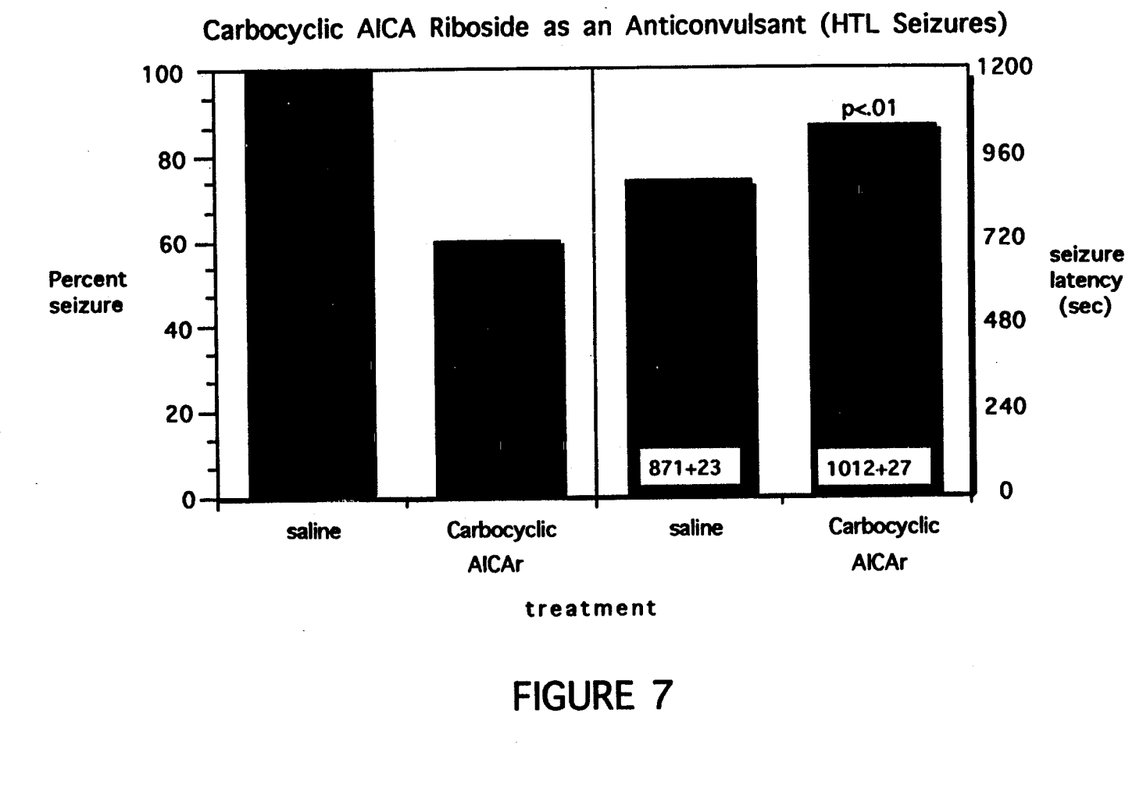
FIG. 7 depicts the activity of carbocyclic AICA riboside in inhibiting HTL induced seizures.

The anti-convulsant properties of carbocyclic AICA riboside are shown in FIG. 7. The seizure latency for carbocyclic AICA riboside treated animals was calculated using only the seizing animals.

We claim:

1. A prodrug of the formula:

wherein $X_1$, $X_2$, and $X_3$ are independently hydrogen, wherein $R_1$ and $R_2$ are independently hydrocarbyl of 1 to about 24 carbon atoms or two of $X_2$ and $X_3$ taken together form a cyclic carbonate group, provided that not all of $X_1$, $X_2$ and $X_3$ are hydrogen.

2. A compound according to claim 1 with the proviso that not all of $X_1$, $X_2$ and $X_3$ are acetyl, propionyl or benzoyl or if one of $X_1$, $X_2$ and $X_3$ is hydrogen, the other two are not both benzoyl.

* * * * *

UNITED STATES PATENT AND TRADEMARK OFFICE
CERTIFICATE OF CORRECTION

PATENT NO. : 5,200,525
DATED : APRIL 6, 1993
INVENTOR(S) : GRUBER, Harry E. et al.

It is certified that error appears in the above-indentified patent and that said Letters Patent is hereby corrected as shown below:

Column 5, lines 13-14, "("+)-5-Amino-1-[Ã-2A-A-dihydroxy-4'"
    should read  --("(+/-)-5-Amino-1-[Ã-2'A-A-dihydroxy-4'--

Signed and Sealed this

Twenty-sixth Day of July, 1994

BRUCE LEHMAN

*Attest:*

*Attesting Officer*            *Commissioner of Patents and Trademarks*